(12) United States Patent  (10) Patent No.: US 7,833,191 B2
Flach et al.  (45) Date of Patent: Nov. 16, 2010

(54) CONTROLLABLE ELECTRODE FOR DEEP BRAIN STIMULATION

(75) Inventors: Erhard Flach, Berlin (DE); Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 34 days.

(21) Appl. No.: 12/401,989

(22) Filed: Mar. 11, 2009

(65) Prior Publication Data
US 2009/0264817 A1 Oct. 22, 2009

(30) Foreign Application Priority Data
Apr. 19, 2008 (DE) .................. 10 2008 019 827

(51) Int. Cl.
*A61M 31/00* (2006.01)
(52) U.S. Cl. .................................... 604/95.05
(58) Field of Classification Search ............ 604/20, 604/21, 95.04, 95.05; 607/116
See application file for complete search history.

(56) References Cited

U.S. PATENT DOCUMENTS

| 5,415,633 | A | * | 5/1995 | Lazarus et al. ........... 604/95.05 |
| 7,130,700 | B2 | * | 10/2006 | Gardeski et al. ............ 607/122 |
| 7,572,257 | B2 | * | 8/2009 | Whayne et al. ............... 606/49 |
| 2004/0097965 | A1 | | 5/2004 | Gardeski et al. |
| 2007/0093710 | A1 | * | 4/2007 | Maschke ................. 600/407 |

FOREIGN PATENT DOCUMENTS

| DE | 4222121 | 9/1993 |
| DE | 100 44 115 | 4/2001 |
| EP | 1395306 | 11/2002 |
| EP | 1 504 713 | 2/2005 |
| FR | 2 732 225 | 10/1996 |
| WO | WO 95/04556 | 2/1995 |

OTHER PUBLICATIONS

German Search Report, dated Dec. 9, 2008.
European Search Report, dated Aug. 21, 2009.

* cited by examiner

*Primary Examiner*—Nicholas D Lucchesi
*Assistant Examiner*—Aarti B Berdichevsky
(74) *Attorney, Agent, or Firm*—ARC IP Law, PC; Joseph J. Mayo

(57) ABSTRACT

Controllable catheter (10) having an elongated shaft (13) which is subdivided into multiple shaft segments, at least two of which are designed as tilt segments (12) and are each connected to at least one adjustment device, so that they can be tilted about a desired tilt angle with respect to the longitudinal axis of the shaft (13), wherein each of the at least one adjustment device is individually controllable and allows individual tilting of a corresponding tilt segment about a desired tilt angle.

14 Claims, 4 Drawing Sheets

CONTROLLABLE ELECTRODE FOR DEEP BRAIN STIMULATION

This application takes priority from German Patent Application DE 10 2008 019 827.7, filed 19 Apr. 2008, the specification of which is hereby incorporated herein by reference.

BACKGROUND OF THE INVENTION

1. Field of the Invention

The invention relates to catheters, in particular leader catheters or stimulation catheters that are used to form a channel in the body tissue of a patient. In particular the present invention relates to those catheters that may be controlled during the formation of a channel in the body of the patient.

2. Description of the Related Art

A number of approaches for controlling catheters are known from the state of the art. There are in particular known catheters which have a tension wire that is guided in the longitudinal direction of the catheter and is attached to its distal end in such a way that a certain longitudinal section of the catheter is curved due to tension on the tension wire.

Such catheters are used especially in the venous or arterial vascular system of a patient or in other body cavities, the path of the catheter on insertion being predetermined primarily by vascular geometry. The controllability of such a catheter serves essentially in the search for certain vascular branches or the search for targeted areas in body cavities.

Catheters designed to form a channel in a patient's body tissue are used, for example, in implantation of electrodes for deep brain stimulation (DBS) in the brain of a patient. On insertion, the catheter must first form the implantation channel in the patient's brain, which is why the path of the catheter is not determined in advance, unlike the situation on insertion into the vascular system of a patient or into body cavities.

Furthermore, the catheter must follow a path that is accurately predetermined by the surgeon in order to save and/or bypass critical tissue areas and regions, for example.

The controllability of traditional catheters is not sufficient for this task; in particular, the radii of curvature of traditional catheters which are adjustable in this context are only inadequately variable and therefore do not allow precise and accurate channel formation. Controllable catheters in the state of the art exert an unacceptable additional normal force on the body tissue—in this case cerebral tissue—precisely when there is a change of direction and a subsequent induction of forward force.

BRIEF SUMMARY OF THE INVENTION

The object of the present invention is thus to make available an instrument that forms channels and allows the formation of an accurate channel in the body tissue of a patient without putting too much strain on the patient, and in particular exerts only tolerable normal forces on the sensitive body tissue during its advance after changing directions.

According to the invention, this object is achieved by a controllable catheter having an elongated shaft, such that the shaft is divided into multiple shaft segments, at least two of which are designed as tilt segments and are each connected to an adjusting device, so that they can be tilted about the axis of the shaft by a desired tilt angle. Each of the adjusting devices can be controlled individually and allows individual tilting of a corresponding tilt segment by a desired tilt angle.

Such a channel-forming instrument makes it possible to tilt first the front tilt segment in the distal direction with the help of its adjusting device and thereby initiate a change of direction of the catheter. In the subsequent further advance of the instrument by the length of the front tilt segment, the tilt segment proximally adjacent to the front tilt segment is designed to follow the channel formed by the front tilt segment and thereby assume the tilt angle of the front tilt segment.

To this end, the tilt segment proximally adjacent to the front tilt segment (hereinafter also referred to as the first) is equipped with a separately controllable adjusting device. The adaptation of the tilt angle of this second tilt segment to the tilt angle of the first tilt segment in the course of the advance causes the inventive catheter to follow the course of the channel already formed as it is advanced and therefore not exert any unnecessary normal forces on the body tissue.

The catheter preferably has a plurality of tilt segments each of which is individually controllable and tiltable. This makes it possible not only for the first proximally adjacent tilt segment to be adjustable after a change in direction but also for the following tilt segments to be adjustable one after the other after any additional advance so that they follow the course of the channel during their advance and thereby prevent an unacceptable normal force from acting on the body tissue.

The adjusting devices of the individual tilt segments are preferably each connected to a control device, which controls the respective setting of the tilt angle and, if necessary, causes the respective adjusting devices to adjust the corresponding tilt angle.

The catheter especially preferably also has a motion sensor which records a shift of the catheter in the distal or proximal directions. It is possible in this way to make an automatic adjustment of the tilt angle of the tilt segments arranged proximally to the first tilt segment after any change of direction and any further advance of the catheter, so that the individual tilt segments follow the channel already formed in the tissue.

The motion sensor is preferably connected to the control unit and designed to record a displacement of the catheter in the proximal direction. Like the adjustment of the tilt segments described above with the advance of the catheter, the catheter is preferably designed to automatically adjust the individual tilt segments as they are retracted.

According to a preferred embodiment variant, the control unit is designed to slowly alter the tilt angle of the tilt segments during the advance or retraction of the catheter.

According to another embodiment of the present invention, the adjusting devices of the individual tilt segments have tension wires and/or tension cables with which the tilt angles of the individual tilt segments can be adjusted.

However, the adjusting devices preferably include piezoelectric actuators with which the tilt angles of the tilt segments can be altered.

The adjusting devices especially preferably have at least two piezoelectric actuators arranged in a ring, each individual one of which is preferably controllable.

In one embodiment as a stimulation catheter, the inventive instrument has at least one tilt segment having an electrode.

According to a preferred embodiment variant, exclusively the front tilt segment in the distal direction is directly controllable by the operator, and the tilting of the other tilt segments is regulated automatically by the control device.

The catheter shaft itself according to various embodiment variants is formed from a tube or a solid elastic material, having a diameter of less than 3.3 mm according to one especially preferred embodiment variant.

According to a preferred embodiment variant, the individual tilt segments are formed by notches or cuts in the shaft material aligned across the longitudinal axis of the catheter.

The adjusting devices which cause the tilt segments to be tilted are preferably accommodated in the notches and/or cuts. These notches and/or cuts preferably have a depth and width which allow a sufficiently small radius of curvature of the catheter at the maximum tilt angle while at the same time ensuring adequate stability of the catheter.

According to various embodiments, the cuts and/or notches may be formed exclusively on one side of the catheter, two sides or more sides or by radial notches. Depending on the embodiment, this results in different degrees of freedom in the controllability of the catheter.

BRIEF DESCRIPTION OF THE DRAWINGS

Additional aspects of the inventive catheter and different embodiment variants are explained in greater detail below on the basis of the drawings, in which.

DETAILED DESCRIPTION OF THE INVENTION

Figure 1:
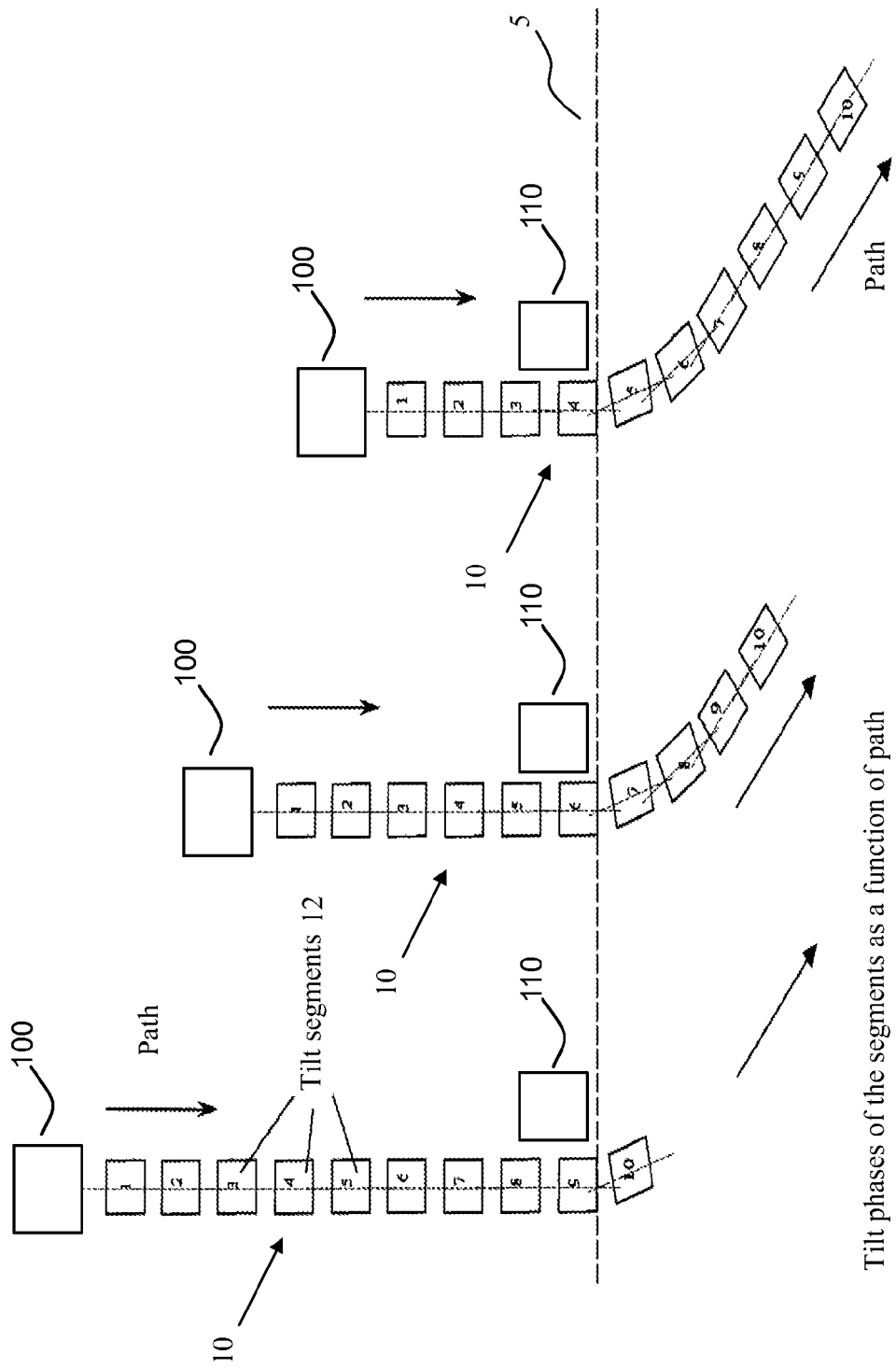
FIGS. 1a, 1b and 1c show three time-shifted schematic diagrams of the catheter for forming a channel in the body tissue of a patient.

FIGS. 1a, 1b and 1c show the inventive catheter 10 in the formation of a curved channel in the body tissue 5 of a patient. The three figures show the inventive catheter 10 in three positions in chronological succession in formation of the channel.

The catheter 10 diagrammed schematically here has a plurality of tilt segments 12.

According to FIG. 1a, a curved channel is formed directly beneath the surface of the body tissue 5. To create a curved channel as the catheter is advanced, the first tilt segment 12 of the catheter 10 arranged on the distal end is already deflected at a tilt angle to the longitudinal axis of the catheter 10.

FIG. 1b shows the remaining advance of the catheter 10 in the body tissue 5 of the patient. As this figure shows, the individual tilt segments of the catheter 10 in the body tissue 5 of the patient are each tilted at a different angle to the longitudinal axis of the catheter 10. Since all tilt segments 12 can be controlled individually, this allows the surgeon an opportunity to form a channel with any desired curvature in the body tissue 5 of a patient. The tilt segments 12 are controllable by means of adjusting devices (not shown here).

It can be seen in FIG. 1b that the catheter 10 has already been advanced in the body tissue 5 of the patient to such an extent that the fourth tilt segment (as seen from the distal end) is already in the position occupied previously by the first tilt segment in FIG. 1a.

The fourth tilt segment as seen from the distal end clearly has the same tilt angle as that assumed by the first tilt segment 12 of the catheter 10 in FIG. 1a. According to FIG. 1a, the first tilt segment 12 of the catheter 10 and the second tilt segment 12 proximally adjacent thereto have different tilt angles with respect to the longitudinal axis of the catheter 10, but FIG. 1b shows that the first tilt segment 12 and the second tilt segment 12 of the catheter 10 proximally adjacent to the former now have the same tilt angle with respect to the longitudinal axis of the catheter.

As shown in FIG. 1c, a further advance of the catheter 10 which according to FIG. 1b has a first and a second tilt segment 12 with the same tilt angle, which means that a straight section of the channel is formed in the body tissue 5 of the patient.

The first tilt segment 12 of the catheter 10 can be controlled and tilted directly by the surgeon. The other tilt segments 12 are automatically aligned by a control unit 100.

The advance of the catheter 12 in the body tissue 5 of a patient is recorded by a motion sensor 110 and forwarded to the control unit 100 connectable to the catheter 10.

The control unit 100 causes all tilt segments 12 situated proximally from the first segment 12 to be aligned so that they follow the curvature of the channel thereby formed during the advance of the catheter.

During the advance of the catheter 10 by the length of a tilt segment 12, a respective tilt segment assumes a tilt angle which is the same as that of the distally adjacent tilt segment 12 at the same location previously occupied in the channel through the tissue.

Figure 2:
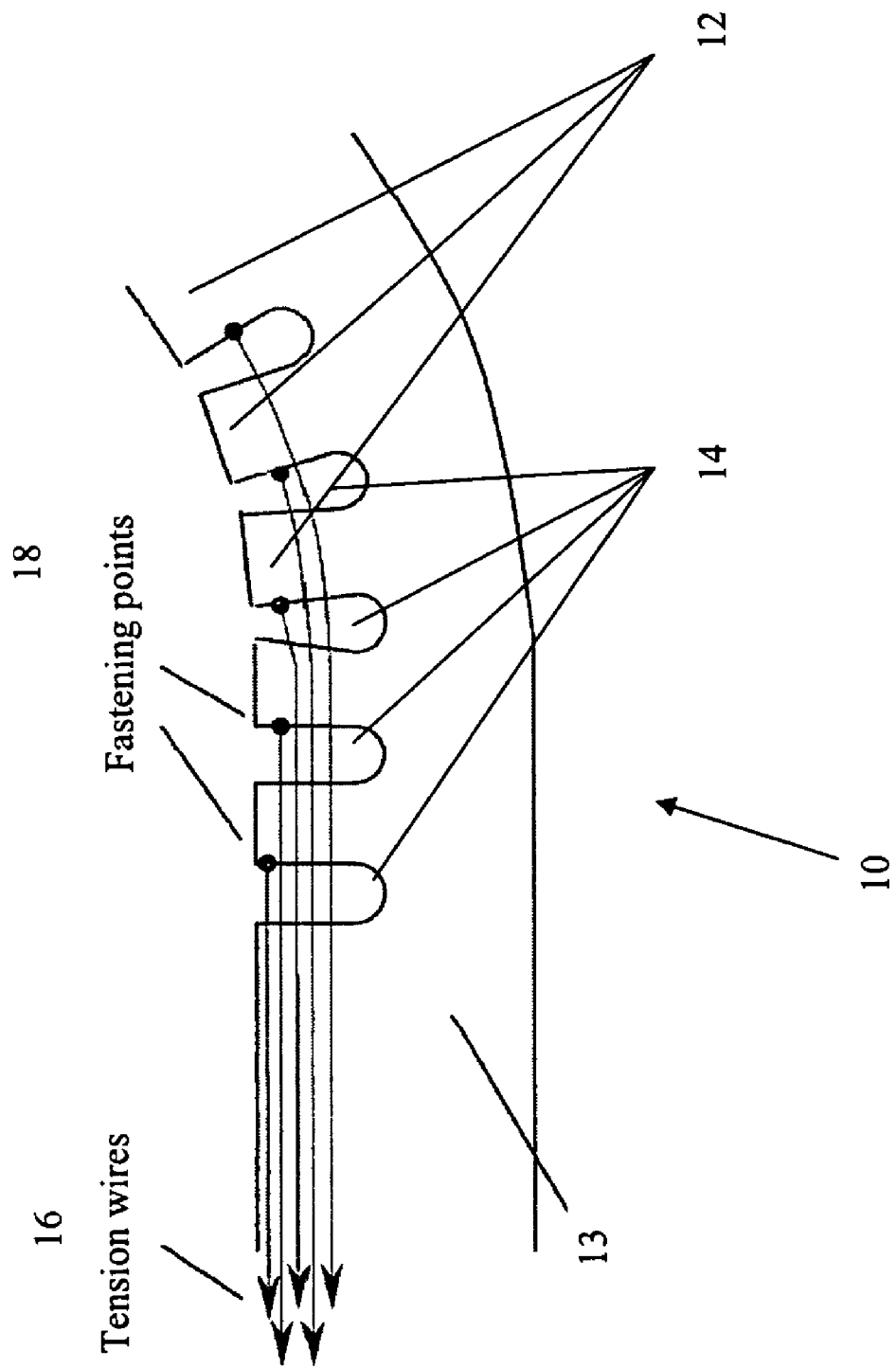
FIG. 2 shows a first embodiment of the inventive catheter with adjusting devices comprising tension wires and tilt segments defined by notches in the catheter shaft.

FIG. 2 shows the inventive catheter 10 according to a first embodiment according to which it has tilt segments which are defined by notches 14 in the catheter shaft 13, arranged across the longitudinal axis of the catheter 10. Each of the tilt segments 12 has fastening points 18 which are connected to a tension wire 16.

Through an appropriate shortening of any tension wire 16, the tilt segment 12 connected to the shortened tension wire 16 is deflected with respect to the longitudinal axis of the catheter 10 at the corresponding fastening point 18. The maximum possible tilt angle, which means the minimum possible radius of a channel to be formed in the tissue 5 of a patient, is determined by the width and depth of the notches 14. As the notches 14 in the catheter shaft 13 of the catheter 10 become wider and deeper, the possible shortening of the tension wires 16 can be greater and the individual tilt segments 12 can be tilted to a greater extent due to the shortening of the tension wires 16. A radius of curvature of the catheter shaft 13 is formed due to the tilting of the tilt segments 12. In the embodiment shown here, the catheter shaft 13 is notched only from one side and is connected laterally to tension wires 16 on only one side toward the catheter axis at fastening points 18, so that only one curvature in one direction is possible with the inventive catheter 10 shown here.

Figure 3:
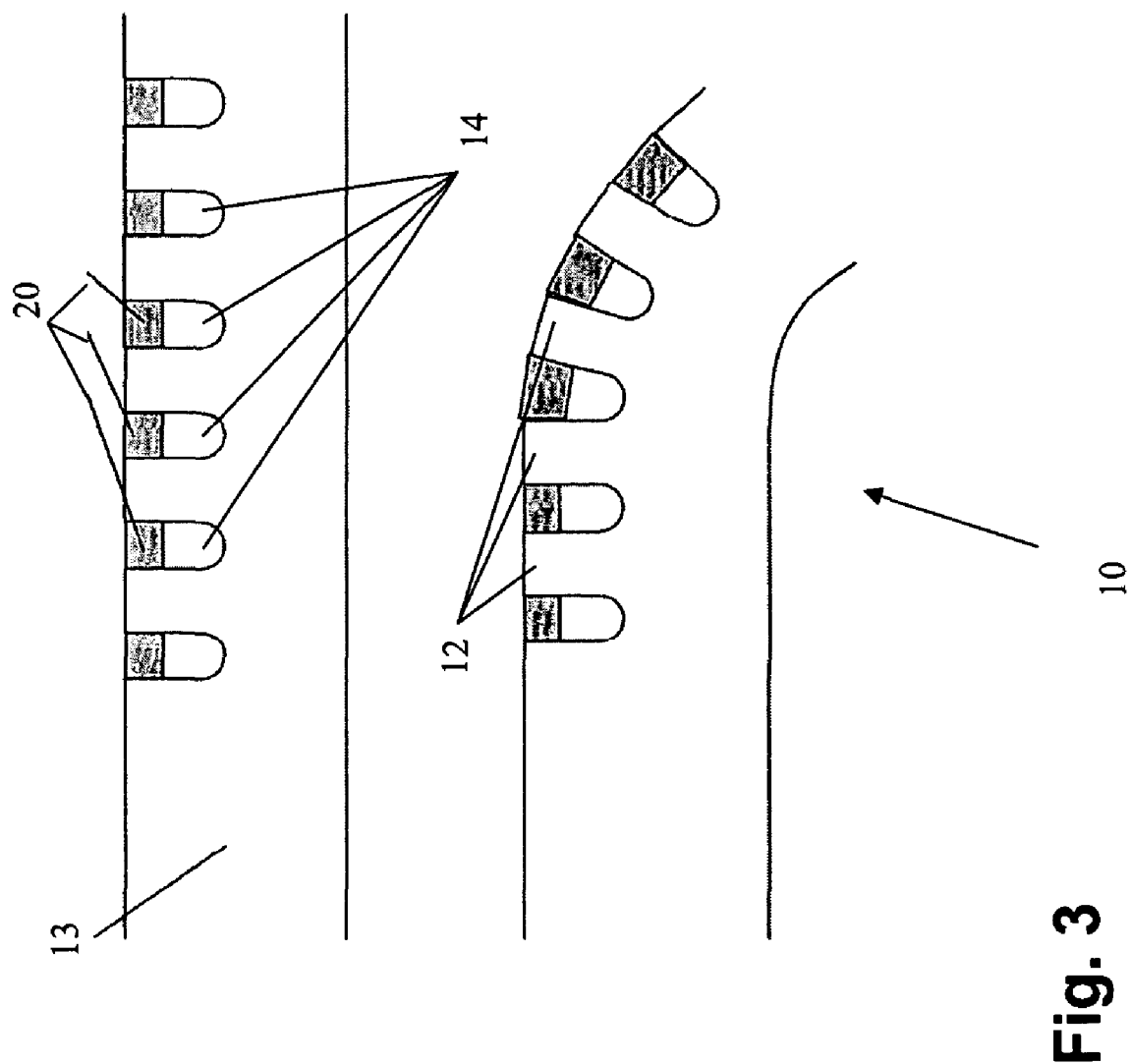
FIG. 3 shows a second embodiment of the inventive catheter with adjusting devices comprising piezostrictive elements and tilt segments defined by notches in the catheter shaft.

The embodiment of the inventive catheter 10 illustrated in FIG. 3 corresponds to the embodiment of the catheter 10 according to FIG. 2 except that the adjusting device here comprises piezostrictive actuators 20 for adjusting the tilt angle of the individual tilt segments 12 of the catheter 10.

Again in this embodiment, all the actuators 20 are controllable individually and allow an adjustment of the corresponding tilt angle of each individual tilt segment 12. Unlike an adjusting device using tension wires, the piezostrictive actuators 20 are designed to be able to widen the notches 14 in the catheter shaft 13 as needed, so that the catheter shaft 13 is bent toward the side of the catheter shaft 13 opposite the notches.

Figure 4:
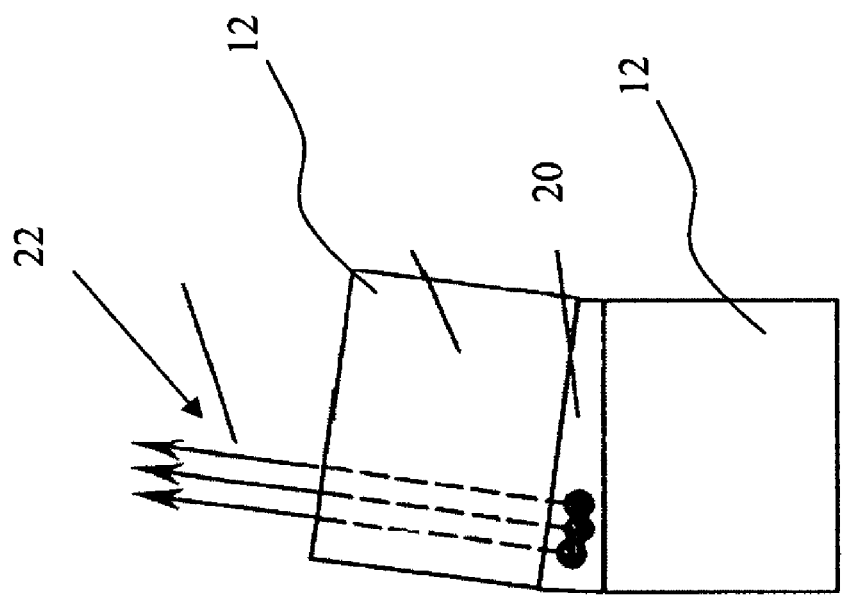
FIG. 4 shows a detailed view of a third embodiment of the inventive catheter having tilt segments that are joined to one another by actuators.

FIG. 4 shows a detailed view of another embodiment of the inventive catheter 10 having cylindrical tilt segments 12 that are connected to one another by cylindrical piezostrictive actuators.

The actuator 20 which is between the two tilt segments 12 can be controlled by several control lines 22, thereby allowing tilting of the tilt segments 12.

What is claimed is:

1. A controllable catheter (10) comprising:
an elongated shaft (13), which is subdivided into multiple shaft segments;
tilt segments (12) of which at least two of the multiple shaft segments are implemented with;
said tilt segments (12) each connected to at least one adjustment device (16, 20), so that said tilt segments (12) can be tilted about a desired tilt angle with respect to a longitudinal axis of the elongated shaft (13);
wherein each of the at least one adjustment device (16, 20) is individually controllable and allows individual tilt of a corresponding tilt segment (12) by the desired tilt angle;
a motion sensor, which records a displacement of catheter (10) in a distal and/or proximal direction;
a control device connected with the at least one adjustment device; and,
wherein said control device is configured to
automatically monitor and adjust a respective setting of tilt angles of individual tilt segments (12) based on an angle of a front segment (12) located in a furthermost distal direction at each said displacement of said elongated shaft (13) in said distal and/or proximal direction as determined by said motion sensor;
set a respective proximal tilt segment (12) to a first tilt angle, that a distally adjacent tilt segment (12) tilted at when said distally adjacent tilt segment was located at a first displacement where the respective proximal tilt segment is currently located at in a tissue channel when said catheter is displaced at a second displacement in the distal direction by a length of a tilt segment (12);
set a respective distal tilt segment (12) to said first tilt angle, that a proximally adjacent tilt segment (12) tilted at when said proximally adjacent tilt segment was located at said second displacement where the respective distal tilt segment is currently located at in a tissue channel when said catheter is displaced at said first displacement in the proximal direction by a length of a tilt segment.

2. The controllable catheter (10) according to claim 1 wherein said control device is further configured to
continuously change tilt angles of the tilt segments (12) while the elongated shaft (13) is displaced.

3. The controllable catheter (10) according to claim 1, wherein said elongated shaft (13) has a diameter of less than 3.3 mm.

4. The controllable catheter (10) according to claim 1, wherein the at least one adjustment device comprises tension wires (16).

5. The controllable catheter (10) according to claim 1, wherein at least one of the tilt segments (12) has at least one electrode.

6. The controllable catheter (10) according to claim 1, device is further configured to:
enable a surgeon to control a tilt of a front segment (12) located in a furthermost distal direction.

7. The controllable catheter (10) according to claim 1, wherein the controllable catheter (10) is a leader catheter.

8. The controllable catheter (10) according to claim 1, wherein the controllable catheter (10) is a stimulation catheter.

9. The controllable catheter (10) according to claim 1, wherein the at least one adjustment device comprises at least one piezoelectric actuator (20).

10. The controllable catheter (10) according to claim 9, wherein each of the at least one adjustment device comprises at least two piezoelectric actuators (20) arranged in a ring.

11. The controllable catheter (10) according to claim 10, wherein each of the at least two piezoelectric actuators (20) is individually controllable.

12. A controllable catheter (10) comprising:
an elongated shaft (13), which is subdivided into multiple shaft segments;
tilt segments (12) of which at least two of the multiple shaft segments are implemented with;
said tilt segments (12) each connected to at least one adjustment device (16, 20), so that said tilt segments (12) can be tilted about a desired tilt angle with respect to a longitudinal axis of the elongated shaft (13);
wherein each of the at least one adjustment device (16, 20) is individually controllable and allows individual tilt of a corresponding tilt segment (12) by the desired tilt angle;
a motion sensor, which records a displacement of catheter (10) in a distal and/or proximal direction;
a control device connected with the at least one adjustment device; and,
wherein said control device is configured to
automatically monitor and adjust a respective setting of tilt angles of individual tilt segments (12) based on an angle of a front segment (12) located in a furthermost distal direction at each said displacement of said elongated shaft (13) in said distal and/or proximal direction as determined by said motion sensor;
set a respective proximal tilt segment (12) to a first tilt angle, that a distally adjacent tilt segment (12) tilted at when said distally adjacent tilt segment was located at a first displacement where the respective proximal tilt segment is currently located at in a tissue channel when said catheter is displaced at a second displacement in the distal direction by a length of a tilt segment (12);
set a respective distal tilt segment (12) to said first tilt angle, that a proximally adjacent tilt segment (12) tilted at when said proximally adjacent tilt segment was located at said second displacement where the respective distal tilt segment is currently located at in a tissue channel when said catheter is displaced at said first displacement in the proximal direction by a length of a tilt segment (12);
continuously change tilt angles of the tilt segments (12) while the elongated shaft (13) is displaced.

13. The controllable catheter (10) according to claim 12, wherein said control device is further configured to:
enable a surgeon to control a tilt of a front segment (12) located in a furthermost distal direction.

14. A controllable catheter (10) comprising:
an elongated shaft (13), which is subdivided into multiple shaft segments;
tilt segments (12) of which at least two of the multiple shaft segments are implemented with;
said tilt segments (12) each connected to at least one adjustment device (16, 20), so that said tilt segments (12) can be tilted about a desired tilt angle with respect to a longitudinal axis of the elongated shaft (13);
wherein each of the at least one adjustment device (16, 20) is individually controllable and allows individual tilt of a corresponding tilt segment (12) by the desired tilt angle;
a motion sensor, which records a displacement of catheter (10) in a distal and/or proximal direction;

a control device connected with the at least one adjustment device; and, wherein said control device is configured to enable a surgeon to control a tilt of a front segment (12) located in a furthermost distal direction;

automatically monitor and adjust a respective setting of tilt angles of remaining tilt segments (12) other than said front segment (12), based on an angle of said front segment at each said displacement of said elongated shaft (13) in said distal and/or proximal direction as determined by said motion sensor;

set a respective proximal tilt segment (12) to a first tilt angle, that a distally adjacent tilt segment (12) tilted at when said distally adjacent tilt segment was located at a first displacement where the respective proximal tilt segment is currently located at in a tissue channel when said catheter is displaced at a second displacement in the distal direction by a length of a tilt segment (12);

set a respective distal tilt segment (12) to said first tilt angle, that a proximally adjacent tilt segment (12) tilted at when said proximally adjacent tilt segment was located at said second displacement where the respective distal tilt segment is currently located at in a tissue channel when said catheter is displaced at said first displacement in the proximal direction by a length of a tilt segment (12);

continuously change tilt angles of the tilt segments (12) while the elongated shaft (13) is displaced.

\* \* \* \* \*